March 25, 1952 M. E. PONTEPRINO Plant Pat. 1,080

AVOCADO TREE

Filed Feb. 9, 1948

Inventor
MEYER E. PONTEPRINO
By Lyon & Lyon Attorneys

Patented Mar. 25, 1952

Plant Pat. 1,080

UNITED STATES PATENT OFFICE 1,080

AVOCADO TREE

Meyer E. Ponteprino, Anaheim, Calif.

Application February 9, 1948, Serial No. 7,127

1 Claim. (Cl. 47—62)

This invention relates to a new and distinctive variety of avocado tree. The new tree was first discovered by applicant in his grove located on Placentia Boulevard, Anaheim, Orange County, California, and its parentage is not known but was produced as a bud variation apparently by natural processes as a sport. The tree and fruit, however, have been established as a definite variety by asexual reproduction by budding upon common varieties of root stock used for the purpose of budding in the propagation of known varieties of avocado trees.

The new variety of avocado tree embodying my invention has been asexually reproduced by budding on ordinary avocado root stock at applicant's grove, located on Placentia Boulevard, Anaheim, Orange County, California.

The new and distinct variety of avocado embodying this invention is characterized by the following distinct characteristics:

(1) The fruit has an exterior skin of distinct color as hereinafter specifically set forth and is generally characterized as a green avocado ripening in the summer time as differentiated from other summer ripening avocados, which are generally designated as having a black or very dark brown skin. The color of the skin of this summer ripening avocado is more comparable with the skin color of the unpatented "Fuerte" avocado ripening in the early spring.

(2) Unlike other summer ripening avocados, the avocado produced by this tree is more nearly pear-shaped and less globular and therein likewise follows more closely the characteristics of the commercially popular "Fuerte" avocado.

(3) The period of maturity of the fruit of this avocado is from June to early October as distinguished from the period of maturity of the ordinary types of light green avocados, which have a period of maturity of from December to early March.

The fruit of this avocado has a very fine texture and a comparatively small seed cavity as illustrated in the accompanying drawing.

Figure 1:
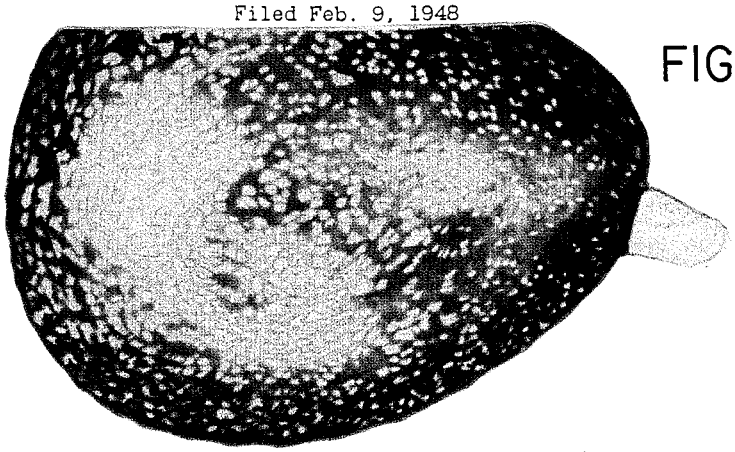

The drawings show in Figure 1 the exterior of the avocado fruit; in

Figure 2:
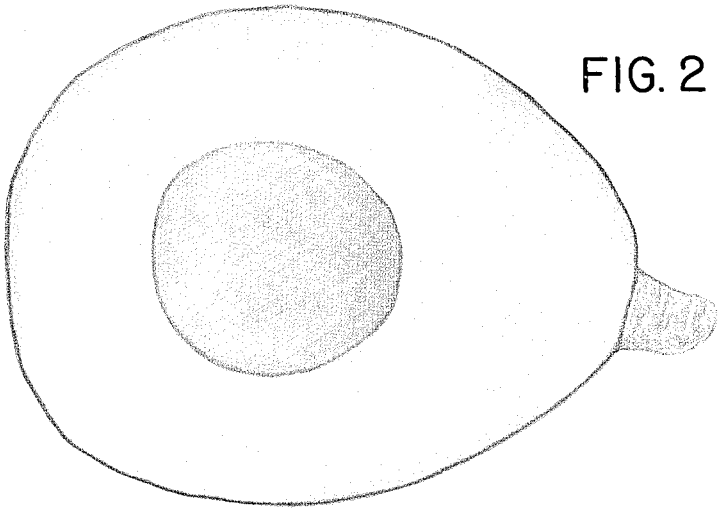
Figure 3:
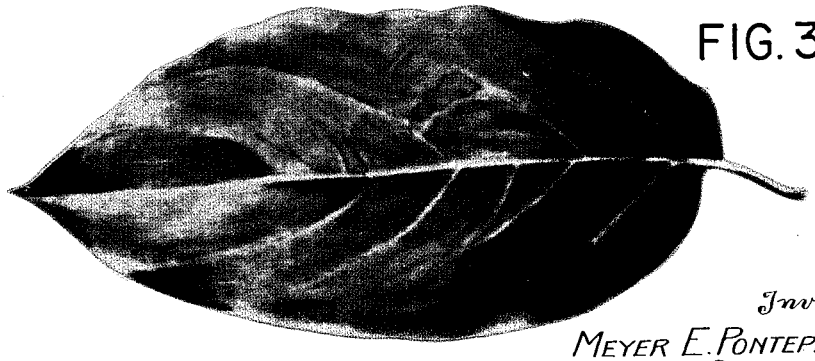

Figure 2 a cut half or section of the fruit with the seed removed showing the seed cavity, and in Figure 3 the leaf of the avocado tree giving the characteristic colors of this avocado, its foliage, meat or pulp, and exterior surface or skin.

In its colors the exterior surface or skin of the fruit is characterized by having a background color as compared with the color plates issued by the Horticultural Color Chart issued by the British Colour Council in collaboration with The Royal Horticultural Society as follows:

The colors in this background are of the parsley green shades comparable with Plates 00962/3, 00962/2, 00962/1, and 00962, tapering to the shades of spinach green comparable with Plates 0960/1 and 0960, and having in its lighter color a color comparable with the fern green Plates 0862/1 and 0862.

The exterior surface is flecked with garnet brown comparable with the color of Plates 009/8/3, 00918/2 and 00918. In its lightest portions the color of the flecks appearing upon the surface of the fruit are lavender green comparable with color Plates 00761/2, 00761/1 and 00761.

The pulp or meat of the inside of the fruit as the same is illustrated in Figure 2 is of a color designated as barium yellow similar to color Plate 503/3 and varying in shades thereof. A typical sample of the avocado produced by this tree has a length from stem end to blossom end of 3½ inches, a width at the blossom end of 1½ inches, and a width at the stem end of ¾ inch. The fruit was partly pear-shaped, as indicated in the drawing, had a weight of 8 ounces, an oil content of 16.63%. This fruit was picked in August, was of the dark green color hereinabove set forth, and the skin peels readily from the flesh and was smooth and was a skin which is classified as medium as distinguished from a thick skin variety of avocado. The fruit varies in size from approximately 8 ounces to 16 ounces per fruit. The flesh of the fruit is of a color comparable with the color designated as barium yellow, as above set forth, carries a noticeable amount of fibre, is of a good flavor, and the flesh does not adhere to the seed. The seed of the typical sample above referred to had a weight of ¾ ounce, had a rough surface, a flesh color, a hard texture, the seed coat was thin, and this coating has a dark brown color tightly adhering to the seed. Applicant is informed that this avocado tree is of the Guatemalan race.

The foliage of the tree is generally of the shape comparable to that of the "Fuerte" avocado tree in that it is generally elongated, of narrow construction showing clearly its vein or stem characteristics upon the surface and is generally of spinach green color shading to a parsley green, the colors being comparable with the plates for spinach green 0960/1 to 0960 and in its parsley green character being comparable with Plates 00962/3, 00962/2, 00962/1 and 00962 in its darkest shading.

I claim:

An avocado tree substantially as described and illustrated characterized in that its fruit is summer ripening, is generally of pear-shape, and is characterized in that the skin of the fruit has a green color shading between parsley green, spinach green and fern green and having flecks upon its surface of garnet brown shading down to a lavender green, and that its interior meat has a barium yellow coloring and further characterized in that the leaf foliage of the tree is the green color of that generally designated as spinach green shading into parsley green color

MEYER E. PONTEPERINO.

REFERENCES CITED

The following references are of record in the file of this patent:

UNITED STATES PATENTS

| Number | Name | Date |
|---|---|---|
| Pl. Pt. 662 | Graham | Nov. 27, 1945 |
| Pl. Pt. 667 | Chenoweth | Jan. 15, 1946 |
| Pl. Pt. 773 | Sherwood | Dec. 30, 1947 |